# (12) United States Patent
Takatsuji et al.

(10) Patent No.: US 7,820,879 B2
(45) Date of Patent: Oct. 26, 2010

(54) USE OF ZINC FINGER TRANSCRIPTION FACTOR ZPT2-3 TO GENERATE PLANTS WITH INCREASED DESICCATION TOLERANCE

(75) Inventors: Hiroshi Takatsuji, Ibaraki (JP); Shoji Sugano, Ibaraki (JP); Hironori Kaminaka, Ibaraki (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 0 days.

(21) Appl. No.: 10/570,037

(22) PCT Filed: Aug. 30, 2004

(86) PCT No.: PCT/JP2004/012464

§ 371 (c)(1), (2), (4) Date: Jun. 19, 2006

(87) PCT Pub. No.: WO2005/024028

PCT Pub. Date: Mar. 17, 2005

(65) Prior Publication Data

US 2006/0272059 A1    Nov. 30, 2006

(30) Foreign Application Priority Data

Sep. 3, 2003    (JP)    ............................ 2003-311535

(51) Int. Cl.
C12N 15/82    (2006.01)
(52) U.S. Cl. ...................................... 800/278; 435/468
(58) Field of Classification Search ........................ None
See application file for complete search history.

(56) References Cited

FOREIGN PATENT DOCUMENTS

WO    WO 2004/058980 A2    7/2004
WO    WO 2005/024028 A1    3/2005

OTHER PUBLICATIONS

Hwang et al. (NCBI, GenBank Sequence Accession No. AF539746, Published Aug. 21, 2003).*
Wells (Biochemistry 29:8509-8517, 1990).*
Ngo et al., (The Protein Folding Problem and Tertiary Structure Prediction, K. Merz., and S. Le Grand (eds.) pp. 492-495,1994).*
Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Takatsuji et al. (NCBI, GenBank, Sequence Accession No. D26086, pp. 1-2, Published Mar. 10, 1995).*
Sugano et.al. (The Plant Journal, 36:830-841, 2003, Applicant's IDS).*
Takatsuji et al. (Plant Cell, 6:947-958, 1994, Applicant's IDS).*
Kasuga et al. (Nature Biotechnology, vol. 17, pp. 287-291, Mar. 1999, Applicant's IDS).*
Kim et al. (The Plant Journal, 25:247-259, 2001, Applicant's IDS).*
van der Krol (Plant Physiology, 121:1153-1162, 1999, Applicant's IDS).*
PCT International Search Report, PCT/JP2004/012464, dated Nov. 22, 2004.
PCT Written Opinion, PCT/JP2004/012464, Nov. 5, 2004.
PCT International Preliminary Examination Report, PCT/JP2004/012464, dated Jul. 15, 2005.
PCT International Preliminary Examination Report, PCT/JP2004/012464, dated Jul. 15, 2005, English translation.
European Search Report, EP 04 77 2420, dated Dec. 4, 2006.
Frugier et al., "A Kruppel-like zinc finger protein is involved in nitrogen-fixing root nodule organogenesis," Genes & Development, 2000, pp. 475-482, vol. 14.
Garg et al., "Trehalose accumulation in rice plants confers high tolerance levels to different abiotic stresses," PNAS, Dec. 10, 2002, pp. 15898-15903, vol. 99, No. 25.
Iida et al., "A zinc finger protein RHL41 mediates the light acclimatization response in *Arabidopsis*," The Plant Journal, 2000, pp. 191-203, vol. 24, No. 2.
Kaminaka et al., "Analysis of Stress-response Profiles of Petunia Zinc-finger Gene, ZPT2-3, Using Luciferase Reporter Gene" Proceedings of the 2001 Annual Meeting and the $41^{st}$ Symposium of the Japanese Society of Plant Physiologists, Mar. 23-26, 2001, pp. 174 (#S322).
Kaminaka et al., "Wound-response Profiles of Petunia Zinc-finger Gene Expression Revealed by Luciferase Reporter Gene," Proceedings of the $17^{th}$ International Conference on Plant Growth Substances, Jun. 1-6, 2001, Poster Session1, pp. 83 (#10).
Kaminaka et al., "Wound-response Profiles of Petunia Zinc-finger Gene, ZPT2-3, Revealed by Luciferase Reporter Gene," Proceedings of the $25^{th}$ Annual Meeting of the Molecular Biology Society of Japan, Dec. 11-14, 2002, pp. 809 (#4P-433).
Kasuga et al., "Improving plant drought, salt, and freezing tolerance by gene transfer of a single stress-inducible transcription factor," Nature Biotechnology, Mar. 1999, pp. 287-291, vol. 17.
Kim et al., "A novel cold-inducible zinc finger protein from soybean, SCOF-1, enhances cold tolerance in transgenic plants," The Plant Journal, 2001, pp. 247-259, vol. 25, No. 3.
Llorente et al., "A novel cold-inducible gene from *Arabidopsis*, RC13, encodes a peroxidase that constitutes a component for stress tolerance," The Plant Journal, 2002, pp. 13-24, vol. 32.
Sugano et al., "Stress-responsive zinc finger gene ZPT2-3 plays a role in drought tolerance in petunia," Plant Journal, Dec. 2003, pp. 830-841, vol. 36.
Takatsuji et al, "Characterization of a zinc finger DNA-binding protein expressed specifically in Petunia petals and seedlings," The EMBO Journal, 1992, pp. 241-249, vol. 11, No. 1.

(Continued)

*Primary Examiner*—Vinod Kumar
(74) *Attorney, Agent, or Firm*—TraskBritt (57) ABSTRACT

To investigate the function of ZPT2-3, petunia transformants overexpressing the ZPT2-3 gene under the control of the CamV 35S promoter were generated to investigate the presence or absence of tolerance against desiccation stress treatment. Surprisingly, petunia plant transformants showed significant tolerance against desiccation as compared to the wild type plants. In addition, neither growth abnormality nor morphological abnormality was observed in petunia plants, and thus overexpression of the ZPT2-3 gene was revealed to have no adverse effects on plant growth.

4 Claims, 2 Drawing Sheets

OTHER PUBLICATIONS

Takatsuji, H., "A single amino acid determines the specificity for the target sequence of two zinc-finger proteins in plants," Biochem. Biophys. Res. Commun., 1996, pp. 219-223, vol. 224.

Takatsuji et al., "A new family of zinc finger proteins in petunia: structure, DNA sequence recognition, and floral organ-specific expression," Plant Cell, 1994, pp. 947-958, vol. 6.

Takatsuji, H., "Zinc-finger proteins: the classical zinc finger emerges in contemporary plant science," Plant Molecular Biology, 1999, pp. 1073-1078, vol. 39.

Van Der Krol et al., "Developmental and Wound-, Cold-, Desiccation-, Ultraviolet-B-Stress-Induced Modulations in the Expression of the Petunia Zinc Finger Transcription Factor Gene ZPT2-2," Plant Physiology, Dec. 1999, pp. 1153-1162, vol. 121.

* cited by examiner

SEQUENCE LISTING

<160> NUMBER OF SEQ ID NOS: 5

<210> SEQ ID NO 1
<211> LENGTH: 2528
<212> TYPE: DNA
<213> ORGANISM: Petunia x hybrida

<400> SEQUENCE: 1

```
actagtggat ccccccctct tgcattagtt aagtgccacg ataccacgaa tatagataca      60
catgaagtta ggtggactgc agaccgaatt aaaggtgcct ctaaccatga tatgttaaca     120
acctaattac ctgatctaca gtaccatatc aaactatttt cttaatctaa ctttccattc     180
aaaattcata ttacgaggtt tgttgtactc tattttcact ggggaggaaa gcttttttaga    240
gatttaacaa aatatatctt catactgtcc agatagtcta aatattcacg tgtagggata     300
ttgatacacc tcattgatga tgcttgtggg gaaaactaag ttgaatccgt tgaacactat     360
gttaacaagc taagtactaa ttaaggagct agtaacatcg tgcgatgcat cactaaaaat     420
tgaatgaacc agcatatcaa gtggagaatg accacctctt tattcgtttg actagaagta     480
catttactat tcattgtatc tatatgtcta tctagagtaa agtagaatca tcatcaagga     540
gtttgaatgc cattctaatt gggtagcttt gcaaaatgag gtagacactc tggttagaat     600
accagctgtg gtccttggta aggaaaatac catgtctctt cccttaaagc cgtcttcaga     660
aataagaaat ggtccattaa tgttaatact gttcaccgag taattaatca cacttatctt     720
atatgactat gcgaagaaat tagataagtc caattggaga aagaggcata tttccaagtc     780
cttttccacca ttttttataa tgtgattgtt tgcaagattc atgcatttat aatggggtga    840
atggcagtag ccgacctttg aatcaaagta aaagttggcg accaattcag tcgcagtcac     900
ctatcgcaac ttggtctta ccttccacac atacacggct gctcctagtt aaagccttct      960
ttatgtgtcc tccaaaaagt cattgcccaa ttggaagaac cttaattaaa tagcgtttaa    1020
aaccgacaaa attaaaataa aatttgtgta ttgttactta atttagaata taaattccat    1080
aactaacgaa aaaagctact cctattacgg agtattaagg aaataggaat agtaaaatca    1140
ccgcgtgggg gcattttgtt tctttcttag tactgttgag ttttgactta gactgagtcc    1200
atagtcaact agtctgcagt ctttgttcac tgactcactc tcctcactaa aatactaagc    1260
ttaggttgct tcctcaccaa gcccacacac ctaaatacaa aatttacttc agtaccactt    1320
gtactttgaa tctaccactt ggcacacaaa tactccttt attttccaac gtgctccact     1380
ccccttcttt atttatattt ttccaattac ttctgtaacc atcttacttt cttattcttt    1440
cccacgcaac ttcccagttc cctctctttc tccccttata tatatctcaa acacattctt    1500
cactctcatt cactcaccaa aacaacttct ctacctcttc tacttgcaca ttcaaattct    1560
ttcattacta cttatctcta ctaatcttga ttcgattta gtaaatcaaa caagagaatc     1620
ttttcagtaa tacaaacaag aaaatttttct ctctatactt gattgagttt agtaaggcaa   1680
acaagaaaac tatcatggca cttgaagcat tgaattctcc aactacaaca acaccaccat    1740
cattccaatt tgagaacaac gggcttaagt accttgagag ttggacaaaa ggtaaaagat    1800
caaaaaggca acgcagcatg gaacgacagt gtactgaaga gagtatttta gcactttgtc    1860
ttatcatgct agcacgtagc gatggttctg ttaataactc acggtctcta ccaccaccac    1920
cactaccacc atcagttcca gtaacgtcgc aaataaacgc gacgttattg gaacagaaga    1980
atttgtacaa gtgttccgtt tgtggtaaag ggtttgggtc ttatcaagct ttaggtggac    2040
```

-continued

```
ataaagcaag tcaccggaaa cttgtcagca tgggaggaga tgaacaatct actacttcca      2100
ctactactaa cgtaacggga actagttccg ctaacgttaa cggtaacgga agaactcacg      2160
aatgttcaat ttgtcacaag tgctttccta ctggacaagc tttaggtggt cataaaaggt      2220
gccactatga cggtggtaac ggtaacggta acggaagtgt aagtgttggg gtgacgtcat      2280
ctgaaggtgt ggggtccact attagtcatc accgtgactt tgacttgaat attcccgcgt      2340
tgccggagtt ttggccggga tttggttccg gcgaggatga ggtggagagt cctcatccag      2400
caaagaagtc aaggctatct cttccaccta aacttgaatt attcaaagga ttatagaggg      2460
aatattgatt tgttacagga agatttatta ggattcacga attttttgtt gactagttta      2520
tgtaatat                                                               2528

<210> SEQ ID NO 2
<211> LENGTH: 1020
<212> TYPE: DNA
<213> ORGANISM: Petunia x hybrida
<220> FEATURE:
<221> NAME/KEY: CDS
<222> LOCATION: (187)..(948)
<223> OTHER INFORMATION:

<400> SEQUENCE: 2
ttcactcacc aaaacaactt ctctacctct tctacttgca cattcaaatt ctttcattac       60
tacttatctc tactaatctt gattcgattt tagtaaatca acaagagaaa tcttttcagt      120
aatacaaaca agaaaatttt ctctctatac ttgattgagt ttagtaaggc aaacaagaaa      180 actatc atg gca ctt gaa gca ttg aat tct cca act aca aca aca cca         228
       Met Ala Leu Glu Ala Leu Asn Ser Pro Thr Thr Thr Thr Pro
       1               5                   10 cca tca ttc caa ttt gag aac aac ggg ctt aag tac ctt gag agt tgg       276
Pro Ser Phe Gln Phe Glu Asn Asn Gly Leu Lys Tyr Leu Glu Ser Trp
15                  20                  25                  30 aca aaa ggt aaa aga tca aaa agg caa cgc agc atg gaa cga cag tgt       324
Thr Lys Gly Lys Arg Ser Lys Arg Gln Arg Ser Met Glu Arg Gln Cys
                35                  40                  45 act gaa gaa gag tat tta gca ctt tgt ctt atc atg cta gca cgt agc       372
Thr Glu Glu Glu Tyr Leu Ala Leu Cys Leu Ile Met Leu Ala Arg Ser
            50                  55                  60 gat ggt tct gtt aat aac tca cgg tct cta cca cca cca cca cta cca       420
Asp Gly Ser Val Asn Asn Ser Arg Ser Leu Pro Pro Pro Pro Leu Pro
        65                  70                  75 cca tca gtt cca gta acg tcg caa ata aac gcg acg tta ttg gaa cag       468
Pro Ser Val Pro Val Thr Ser Gln Ile Asn Ala Thr Leu Leu Glu Gln
    80                  85                  90 aag aat ttg tac aag tgt tcc gtt tgt ggt aaa ggg ttt ggg tct tat       516
Lys Asn Leu Tyr Lys Cys Ser Val Cys Gly Lys Gly Phe Gly Ser Tyr
95                  100                 105                 110 caa gct tta ggt gga cat aaa gca agt cac cgg aaa ctt gtc agc atg       564
Gln Ala Leu Gly Gly His Lys Ala Ser His Arg Lys Leu Val Ser Met
                115                 120                 125 gga gga gat gaa caa tct act act tcc act act act aac gta acg gga       612
Gly Gly Asp Glu Gln Ser Thr Thr Ser Thr Thr Thr Asn Val Thr Gly
            130                 135                 140 act agt tcc gct aac gtt aac ggt aac gga aga act cac gaa tgt tca       660
Thr Ser Ser Ala Asn Val Asn Gly Asn Gly Arg Thr His Glu Cys Ser
        145                 150                 155 att tgt cac aag tgc ttt cct act gga caa gct tta ggt ggt cat aaa       708
Ile Cys His Lys Cys Phe Pro Thr Gly Gln Ala Leu Gly Gly His Lys
```

```
            160                 165                 170
agg tgc cac tat gac ggt ggt aac ggt aac ggt aac gga agt gta agt     756
Arg Cys His Tyr Asp Gly Gly Asn Gly Asn Gly Asn Gly Ser Val Ser
175                 180                 185                 190 gtt ggg gtg acg tca tct gaa ggt gtg ggg tcc act att agt cat cac     804
Val Gly Val Thr Ser Ser Glu Gly Val Gly Ser Thr Ile Ser His His
                195                 200                 205 cgt gac ttt gac ttg aat att ccc gcg ttg ccg gag ttt tgg ccg gga     852
Arg Asp Phe Asp Leu Asn Ile Pro Ala Leu Pro Glu Phe Trp Pro Gly
        210                 215                 220 ttt ggt tcc ggc gag gat gag gtg gag agt cct cat cca gca aag aag     900
Phe Gly Ser Gly Glu Asp Glu Val Glu Ser Pro His Pro Ala Lys Lys
            225                 230                 235 tca agg cta tct ctt cca cct aaa ctt gaa tta ttc aaa gga tta tag     948
Ser Arg Leu Ser Leu Pro Pro Lys Leu Glu Leu Phe Lys Gly Leu
                240                 245                 250 agggaatatt gatttgttac aggaagattt attaggattc acgaattttt tgttgactag   1008
tttatgtaat at                                                       1020

<210> SEQ ID NO 3
<211> LENGTH: 253
<212> TYPE: PRT
<213> ORGANISM: Petunia x hybrida

<400> SEQUENCE: 3

Met Ala Leu Glu Ala Leu Asn Ser Pro Thr Thr Thr Pro Pro Ser
1               5                   10                  15

Phe Gln Phe Glu Asn Asn Gly Leu Lys Tyr Leu Glu Ser Trp Thr Lys
            20                  25                  30

Gly Lys Arg Ser Lys Arg Gln Arg Ser Met Glu Arg Gln Cys Thr Glu
        35                  40                  45

Glu Glu Tyr Leu Ala Leu Cys Leu Ile Met Leu Ala Arg Ser Asp Gly
    50                  55                  60

Ser Val Asn Asn Ser Arg Ser Leu Pro Pro Pro Leu Pro Pro Ser
65                  70                  75                  80

Val Pro Val Thr Ser Gln Ile Asn Ala Thr Leu Leu Glu Gln Lys Asn
                85                  90                  95

Leu Tyr Lys Cys Ser Val Cys Gly Lys Gly Phe Gly Ser Tyr Gln Ala
            100                 105                 110

Leu Gly Gly His Lys Ala Ser His Arg Lys Leu Val Ser Met Gly Gly
        115                 120                 125

Asp Glu Gln Ser Thr Thr Ser Thr Thr Thr Asn Val Thr Gly Thr Ser
    130                 135                 140

Ser Ala Asn Val Asn Gly Asn Gly Arg Thr His Glu Cys Ser Ile Cys
145                 150                 155                 160

His Lys Cys Phe Pro Thr Gly Gln Ala Leu Gly Gly His Lys Arg Cys
                165                 170                 175

His Tyr Asp Gly Gly Asn Gly Asn Gly Asn Gly Ser Val Ser Val Gly
            180                 185                 190

Val Thr Ser Ser Glu Gly Val Gly Ser Thr Ile Ser His His Arg Asp
        195                 200                 205

Phe Asp Leu Asn Ile Pro Ala Leu Pro Glu Phe Trp Pro Gly Phe Gly
    210                 215                 220

Ser Gly Glu Asp Glu Val Glu Ser Pro His Pro Ala Lys Lys Ser Arg
225                 230                 235                 240
```

```
Leu Ser Leu Pro Pro Lys Leu Glu Leu Phe Lys Gly Leu
                245                 250

<210> SEQ ID NO 4
<211> LENGTH: 33
<212> TYPE: DNA
<213> ORGANISM: Artificial
<220> FEATURE:
<223> OTHER INFORMATION: An artificially synthesized oligonucleotide

<400> SEQUENCE: 4
ctagaggatc caacaatggc acttgaagca ttg                               33

<210> SEQ ID NO 5
<211> LENGTH: 33
<212> TYPE: DNA
<213> ORGANISM: Artificial
<220> FEATURE:
<223> OTHER INFORMATION: An artificially synthesized oligonucleotide

<400> SEQUENCE: 5
aattcaatgc ttcaagtgcc attgttggat cct                               33
```

USE OF ZINC FINGER TRANSCRIPTION FACTOR ZPT2-3 TO GENERATE PLANTS WITH INCREASED DESICCATION TOLERANCE

TECHNICAL FIELD

The present invention relates to uses of the zinc finger transcription factor ZPT2-3 to generate plants with increased desiccation tolerance, and mainly belongs to the field of plant breeding.

BACKGROUND ART

Plant desiccation tolerance is an important factor that relates to the labor reduction in cultivation of various crops and garden plants and to the expansion of cultivable areas. If improvement of desiccation tolerance by genetic engineering can overcome the difficulties in crop cultivation in arid regions, the possibility of it as a countermeasure against world food shortage can be expected. Previous reports of experimental examples in which desiccation tolerance was improved by genetic recombination include enhanced trehalose synthesis (Non-Patent Document 2: Garg et al., (2002) Proc. Natl. Acad. Sci. USA 99, 15898-15903) and introduction of the peroxidase gene (Non-Patent Document 6: Llorente et al., (2002) Plant J. 32, 13-24). Moreover, an example of increasing desiccation tolerance with the use of transcription factor genes is introduction of the DREB gene comprising an AP2 domain (Non-Patent Document 4: Kasuga et al., (1999) Nat Biotechnol 17, 287-291).

ZPT2-3 (renamed from EPF2-7) is a zinc finger transcription factor of *Petunia hybrida* (petunia). The present inventors previously isolated the ZPT2-3 gene from petunia and found that it was specifically expressed in floral organs; however, its function remained unclear (Non-Patent Document 7: Takatsuji et al., (1994) Plant Cell 6, 947-958). Recently, it was found that wounding, low temperature, and treatment with heavy metals induce the expression of ZPT2-3 gene and that a jasmonic acid-mediated signaling pathway is involved in the induction of the expression. At the same time, it was also found that in adult leaves, the expression of the gene was not induced in response to desiccation treatment or high salt concentration (Non-Patent Document 9: The Japanese Society of Plant Physiologists, Annual Meeting in 2001 Abstracts; Non-Patent Document 10: 25th Annual Meeting of the Molecular Biology Society of Japan). Soybean SCOF-1 that confers freezing tolerance (Non-Patent Document 5: Kim et al., (2001) Plant J. 25, 247-259), *Arabidopsis thaliana* RHL41 that confers tolerance to high-intensity light (Non-Patent Document 3: Iida et al., (2000) Plant J. 24, 191-203), and *Medicago sativa* Mszpt2-1 involved in nodulation (Non-Patent Document 1: Frugier et al., (2000) organogenesis. Genes Dev. 14, 475-482) are known as structurally similar zinc finger genes. However, zinc finger genes that confer desiccation tolerance when introduced into plants are still unknown.

Non-Patent Document 1: Frugier et al., (2000) organogenesis. Genes Dev. 14, 475-482.
Non-Patent Document 2: Garg et al., (2002) Proc. Natl. Acad. Sci. USA 99, 15898-15903.
Non-Patent Document 3: Iida et al., (2000) Plant J. 24, 191-203.
Non-Patent Document 4: Kasuga et al., (1999) Nat Biotechnol 17, 287-291.
Non-Patent Document 5: Kim et al., (2001) Plant J. 25, 247-259.
Non-Patent Document 6: Llorente et al., (2002) Plant J. 32, 13-24.
Non-Patent Document 7: Takatsuji et al., (1994) Plant Cell 6, 947-958.
Non-Patent Document 8: Takatsuji et al., (1992) EMBO J. 11, 241-249.
Non-Patent Document 9: The Japanese Society of Plant Physiologists, Annual Meeting in 2001 and the 41st Symposium, Abstracts p. 174
Non-Patent Document 10: 25th Annual Meeting of the Molecular Biology Society of Japan, Program and Abstracts p. 809

DISCLOSURE OF THE INVENTION

The present invention was achieved in view of the circumstances described above. An objective of the present invention is to increase desiccation tolerance of plants using a zinc finger transcription factor gene.

To clarify the function of ZPT2-3, the present inventors generated petunia transformants overexpressing the ZPT2-3 gene under the control of the CaMV 35S promoter to investigate the presence or absence of tolerance against desiccation stress treatment. Surprisingly, results indicated that petunia transformants showed significant tolerance against desiccation as compared with the wild type plants. In addition, neither growth abnormality nor morphological abnormality was observed in the petunia transformants, and thus overexpression of the ZPT2-3 gene was revealed to have no adverse effects on plant growth or such. Specifically, the present inventors found that the desiccation stress tolerance of plants can be increased efficiently by expressing the ZPT2-3 gene in plants, and thus achieved the present invention.

The present invention relates to uses of a zinc finger transcription factor-encoding gene to increase plant desiccation tolerance. More specifically, the present invention provides:

[1] an agent for increasing plant desiccation tolerance, which comprises the DNA of any one of (a) to (d), or a vector into which the DNA is inserted:
(a) a DNA encoding a protein comprising the amino acid sequence of SEQ ID NO: 3;
(b) a DNA comprising the coding region of the nucleotide sequence of SEQ ID NO: 1 or 2;
(c) a DNA that hybridizes under stringent conditions to a DNA comprising the nucleotide sequence of SEQ ID NO: 1 or 2; and
(d) a DNA encoding a protein comprising an amino acid sequence with a substitution, deletion, addition, and/or insertion of one or more amino acids in the amino acid sequence of SEQ ID NO: 3;

[2] a transformed plant cell capable of being regenerated into a plant with increased desiccation tolerance, wherein the DNA of any one of (a) to (d), or a vector into which the DNA is inserted, is introduced into the cell:
(a) a DNA encoding a protein comprising the amino acid sequence of SEQ ID NO: 3;
(b) a DNA comprising the coding region of the nucleotide sequence of SEQ ID NO: 1 or 2;
(c) a DNA that hybridizes under stringent conditions to a DNA comprising the nucleotide sequence of SEQ ID NO: 1 or 2; and
(d) a DNA encoding a protein comprising an amino acid sequence with a substitution, deletion, addition, and/or insertion of one or more amino acids in the amino acid sequence of SEQ ID NO: 3;

[3] a plant with increased desiccation tolerance, which is regenerated from the transformed plant cell of [2];

[4] a plant with increased desiccation tolerance, which is a progeny or a clone derived from the plant of [3];

[5] a breeding material for the plant of [3] or [4]; and

[6] a method for producing a plant with increased desiccation tolerance, which comprises the steps of:

(I) introducing the DNA of any one of (a) to (d), or a vector into which the DNA is inserted, into a plant cell:
(a) a DNA encoding a protein comprising the amino acid sequence of SEQ ID NO: 3;
(b) a DNA comprising the coding region of the nucleotide sequence of SEQ ID NO: 1 or 2;
(c) a DNA that hybridizes under stringent conditions to a DNA comprising the nucleotide sequence of SEQ ID NO: 1 or 2; and
(d) a DNA encoding a protein comprising an amino acid sequence with a substitution, deletion, addition, and/or insertion of one or more amino acids in the amino acid sequence of SEQ ID NO: 3; and
(II) regenerating a plant from the transformed plant cell into which the vector has been introduced in step (I).

BRIEF DESCRIPTION OF THE DRAWINGS

(a) ZPT2-3 gene expressions in wild-type (WT) and 35S::ZPT2-3-transformed petunia plants (#1 to #36) are shown. Hybridization was performed using labeled antisense ZPT2-3 RNA. Among the transformants, nine lines, #5, 6, 14, 22, 24, 33, 34, 35, and 36, expressed the introduced ZPT2-3 gene at high levels.

(b) Plants after watering was stopped for two weeks and resumed for one week. Wild type dried up and died without recovery, while the transformants recovered and grew again normally.

BEST MODE OF CARRYING OUT THE INVENTION

The present invention provides agents for increasing plant desiccation tolerance using a zinc finger transcription factor-encoding gene.

In the present invention, the phrase "increase plant desiccation tolerance" means increasing the desiccation tolerance in subject plants in comparison with the wild type plants. As shown in Example 5, whether an agent comprising a particular gene induces desiccation tolerance in plants can be evaluated by the steps of: cultivating wild-type plants and plants in which the gene comprised in the agent is expressed, stopping watering for a certain period of time, resuming watering, and investigating the survival rate of the plants.

A suitable example of the zinc finger transcription factor gene as an active ingredient of agents of the present invention is a DNA encoding the petunia-derived ZPT2-3 protein (SEQ ID NO: 3). In particular, for example, DNAs comprising the coding region of the nucleotide sequence of SEQ ID NO: 1 or 2 can be preferably used in the present invention.

There is no particular limitation on the type of DNAs used for the agents of the present invention which confer desiccation tolerance to plants, and the DNAs may be cDNAs or genomic DNAs. Genomic DNAs and cDNAs can be prepared by conventional methods known to those skilled in the art. For example, genomic DNA can be prepared by: designing an appropriate primer pair based on the known nucleotide sequence information on zinc finger genes; carrying out PCR using genomic DNAs prepared from a plant of interest as template; and screening genomic libraries using the amplified DNA fragment as a probe. Alternatively, zinc finger transcription factor-encoding cDNAs can be prepared by: designing a primer pair as shown above; carrying out PCR using cDNA or mRNA prepared from a plant of interest as template; and screening cDNA libraries using the amplified DNA fragment as a probe. Moreover, DNAs of interest can also be synthesized by using commercially available DNA synthesizers.

DNAs encoding a protein structurally similar to the petunia-derived ZPT2-3 protein (SEQ ID NO: 3) (for example, mutants, derivatives, alleles, variants, and homologues thereof) may be used as an active ingredient in the agents of the present invention, as long as they have the function of increasing plant desiccation tolerance. Such DNAs include, for example, DNAs encoding a protein comprising an amino acid sequence with a substitution, deletion, addition, and/or insertion of one or more amino acids in the amino acid sequence of SEQ ID NO: 3.

Methods that are well known to those skilled in the art for preparing DNAs encoding proteins whose amino acid sequences have been altered include, for example, site-directed mutagenesis (Kramer, W. & Fritz, H. -J. (1987) "Oligonucleotide-directed construction of mutagenesis via gapped duplex DNA", Methods in Enzymology, 154: 350-367) and such. Mutations in protein amino acid sequences may also occur in nature due to mutations in the nucleotide sequences that encode the proteins. Accordingly, DNAs of the present invention also include DNAs that encode proteins comprising an amino acid sequence with a substitution, deletion, addition, and/or insertion of one or more amino acids in the amino acid sequence encoding a naturally occurring ZPT2-3 protein (SEQ ID NO: 3), as long as they encode a protein functionally equivalent to the naturally occurring protein. There is no limitation on the number of amino acids to be altered, as long as the altered protein has the function of increasing plant desiccation tolerance. Typically 50 amino acids or less, preferably 30 amino acids or less, and more preferably ten amino acids or less (for example, five amino acids or less, or three amino acids or less) are altered. Preferred amino acid alterations are conservative substitutions. The hydropathic index (Kyte and Doolittle, J Mol Biol. May 5, 1982; 157(1):105-32) and hydrophilicity value (U.S. Pat. No. 4,554,101) for each amino acid before and after alteration are preferably within ±2, more preferably within ±1, and most preferably within ±0.5.

Even if a nucleotide sequence is mutated, the mutation does not necessarily result in an amino acid mutation in the protein (silent mutations). The DNAs of the present invention also comprise such silent mutants.

For DNAs encoding a protein structurally similar to the petunia-derived ZPT2-3 protein (SEQ ID NO: 3), those prepared by hybridization techniques (Southern, E. M. (1975) Journal of Molecular Biology, 98, 503) or polymerase chain reaction (PCR) techniques (Saiki, R. K. et al. (1985) Science, 230, 1350-1354; Saiki, R. K. et al. (1988) Science, 239, 487-491) can be used. Specifically, the DNAs of the present invention include DNAs that hybridize under stringent conditions with DNAs comprising the nucleotide sequence of SEQ ID NO: 1 or 2. To isolate such DNAs, the hybridization reaction is preferably carried out under stringent conditions. Herein, the "stringent conditions" refers to hybridization conditions of 6 M urea, 0.4% SDS, and 0.5×SSC, or those with equivalent stringency, but is not limited thereto. DNAs with higher homology can be expected to be isolated when conditions of higher stringency, for example, conditions of 6 M urea, 0.4% SDS, and 0.1×SSC, are used. There exist multiple factors that influence hybridization stringency, such as temperature and salt concentration. Those skilled in the art can appropriately select such factors to achieve optimal stringency. DNAs isolated by the procedure described above are expected to have high homology to the amino acid sequence of the petunia-derived ZPT2-3 protein (SEQ ID NO: 3) at the amino acid level. The term "high homology" refers to at least 50% or higher sequence identity, more preferably 70% or higher sequence identity, still more preferably 90% or higher sequence identity (for example, 95%, 96%, 97%, 98%, 99%, or higher sequence identity) in the entire amino acid sequence. Such amino acid sequence or nucleotide sequence identity can be determined using the BLAST algorithm by Karin and Altschul (Proc. Natl. Acad. Sci. USA 87:2264-2268, 1990; Proc Natl Acad Sci USA 90: 5873, 1993). Programs called BLASTN and BLASTX have been developed based on the BLAST algorithm (Altschul S F, et al., J Mol Biol 215: 403, 1990). When nucleotide sequences are analyzed using the BLASTN program, parameters may be set to, for example, score=100 and wordlength=12. Alternatively, when amino acid sequences are analyzed using the BLASTX program, parameters may be set to, for example, score=50 and wordlength=3. When the BLAST or Gapped BLAST program is used, default parameters for each program are used. Specific procedures for these analytical methods are known.

There is no particular limitation on the type of vectors to which the DNAs described above are inserted, as long as the vectors allow expression of the inserted genes in plant cells. It is possible to use, for example, vectors having a promotor (for example, the 35S promoter of cauliflower mosaic virus) for constitutive gene expression in plant cells or vectors having a promoter induced to activate upon external stimulation. Such vectors to which the DNAs described above are inserted can be introduced into plant cells by conventional methods known to those skilled in the art, for example, the polyethylene glycol method, electroporation, the Agrobacterium-mediated method, or the particle gun method. When the Agrobacterium-mediated method is used, the DNAs described above can be introduced into plant cells, for example, by inserting the above-described DNA into an expression vector; introducing the vector into Agrobacteria; and infecting plants cells with the Agrobacteria by direct infection or leaf disk inoculation, according to the method of Nagel et al., (Microbiol. Lett., 67:325 (1990)).

The term "agents" of the present invention may be the DNAs described above, vectors into which the DNAs have been inserted, or mixtures thereof comprising other ingredients for introduction into plant cells. For example, the DNAs described above, the vectors into which the above-described DNAs have been inserted, Agrobacteria into which the above-described DNAs have been introduced, and biochemical reagents and solutions comprising them are also comprised in the agents of the present invention.

The present invention provides transformed plant cells into which the DNAs or vectors described above have been introduced and which can be regenerated into plants with increased desiccation tolerance. The transformed plant cells of the present invention can be in any form, as long as they are plant cells or groups of cells into which the DNAs or vectors described above have been introduced and that can regenerate into plants. For example, suspension culture cells, protoplasts, leaf discs, calluses, and such are comprised in the plant cells of the present invention.

The present invention provides plants that have increased desiccation tolerance and were regenerated from the above-described transformed cells. The phrase "plants with increased desiccation tolerance" in the present invention refers to plants whose desiccation tolerance has been artificially increased as compared to the wild-type plants.

The present invention provides not only plants regenerated from cells into which the above-described DNAs have been introduced, but also progenies and clones thereof. Once a transformed plant whose genome has been introduced with the DNAs or vectors described above is generated, progenies or clones thereof can be obtained from the plant through sexual or asexual reproduction. When breeding materials (for example, seeds, fruits, cut panicles, tubers, tuberous roots, springs, calluses, and protoplasts) are prepared from the plant, progenies or clones thereof, the plant can be produced on a large scale from these materials.

The present invention further provides methods for producing plants with increased desiccation tolerance. The production methods comprise the steps of introducing the DNAs or vectors described above into plant cells, and regenerating plants from the cells into which the DNAs or vectors described above have been introduced.

The step of regenerating plants from plant cell transformants can be achieved by conventional art-known methods appropriate for each plant type. For example, for petunia, the shoot is regenerated on culture plates comprising auxin (indole acetic acid, IAA) and cytokinin (benzylaminopurine, BAP), and rooted and grown on culture plates comprising indole butyric acid (IBA) (van der Meer, I. M. (1999), Methods Mol Biol 111, 327-334). Torenia, tobacco, and gerbera plants can also be regenerated by methods similar to that described above (Elomaa, P., Mehto, M., Kotilainen, M., Helariutta, Y., Nevalainen, L., and Teeri, T. H. (1998) Plant J 16, 93-109). Methods for regenerating other plants include, for example, the method of Fujimura et al. (Plant Tissue Culture Lett. 2:74 (1995)) for rice; the methods of Shillito et al. (Bio/Technology 7:581 (1989)) and Gorden-Kamm et al. (Plant Cell 2:603(1990)) for maize; the method of Visser et al. (Theor. Appl. Genet 78:594 (1989)) for potato; the method of Akama et al. (Plant Cell Reports 12:7-11 (1992)) for *Arabidopsis thaliana*; and the method of Doi et al. (Japanese Patent Application Kokai Publication No. (JP-A) H8-89113 (unexamined, published Japanese patent application)) for Eucalyptus.

EXAMPLES

Example 1

Isolation and Expression of ZPT2-3 Gene

ZPT2-3 gene (renamed from EPF2-7) was isolated (Takatsuji et al., (1994) Plant Cell 6, 947-958) using the cDNA of another zinc finger gene EPF1 isolated previously (Takatsuji et al., (1992) EMBO J. 11, 241-249) as a probe to screen a petunia genomic DNA library. The nucleotide sequence of the isolated gene is shown in SEQ ID NO: 1. The expression of this gene is found to be induced by wounding, low temperature, and heavy metal (Cd, Ni, Cu, or Zn). Meanwhile, the expression was induced by neither desiccation nor salt treatment in experiments using adult leaves.

Example 2

Figure 1:
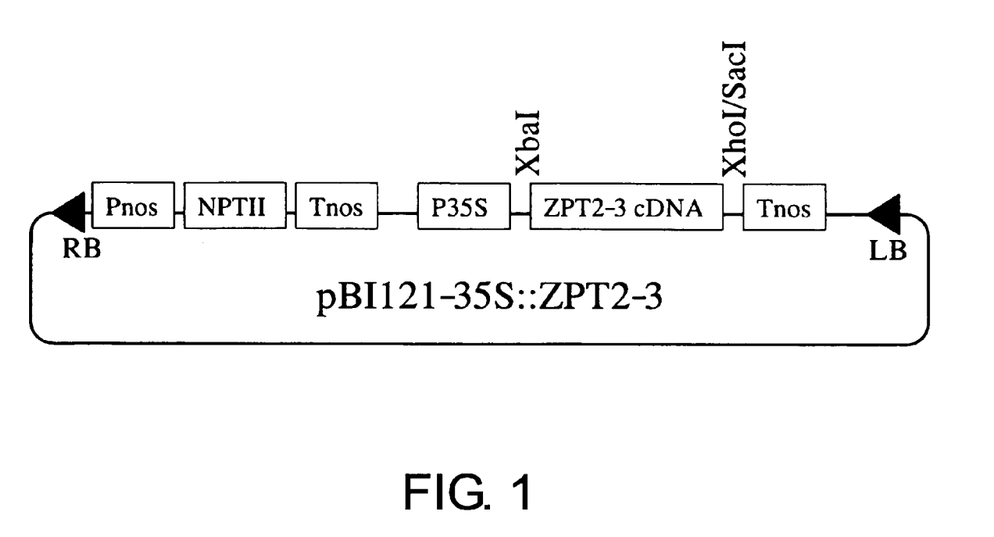
FIG. 1 is a diagram showing the construction of a ZPT2-3 expression vector.

Construction of a Plant Expression Vector That Comprises ZPT2-3-encoding Polynucleotide A vector for constitutive expression of the ZPT2-3 gene in plants was prepared by the following procedure. To the XbaI-EcoRI site (on the 5' side of ZPT2-3 sequence) of a pBluescript vector (purchased from Stratagene) comprising a ZPT2-3 gene sequence, in which the sequence around its translation initiation site has been deleted, complementary oligo DNAs (top strand: 5'-CTAGAGGATCCAACAATGGCACT-TGAAGCATTG-3'/SEQ ID NO: 4, and bottom strand: AAT-TCAATGCTTCAAGTGCCATTGTTGGATCCT/SEQ ID NO: 5; which are annealed to each other) encoding a sequence corresponding to the above deleted sequence was inserted to prepare a DNA comprising the entire coding region of the ZPT2-3 gene (pBS-ZPT2-7F). Then, pBS-ZPT2-7F was digested with XhoI, blunted with T4 DNA polymerase, and digested with XbaI. The resulting DNA fragment was inserted into an XbaI-SacI (blunt) site, which is located between the 35S promoter and the Nos terminator on pBI121 (purchased from Clontech). As shown in FIG. 1, the constructed vector for ZPT2-3 gene overexpression (pBI121-35S::ZPT2-3) comprises the CaMV 35S promoter region (P35S; 0.8 kb), a polynucleotide (ZPT2-3; 0.8 kb) encoding the ZPT2-3 cDNA of the present invention, and the terminator region of nopaline synthase (Tnos; 0.3 kb). The nucleotide sequence of the ZPT2-3 cDNA is shown in SEQ ID NO: 2.

Example 3

Introduction of the fusion gene into petunia cells (1) *Agrobacterium tumefaciens* LBA4404 (purchased from Clontech) was cultured in L medium containing 250 μg/ml streptomycin and 50 μg/ml rifampicin at 28° C. Cell suspension was prepared according to the method described by Nagel et al. (Microbiol. Lett.(1990). 67,325), and the plasmid vector constructed in Example 2 was introduced into the bacterial cells by electroporation.

(2) Introduction of the polynucleotide encoding each fusion gene into petunia cells *Agrobacterium tumefaciens* LBA4404 obtained in (1) was cultured in YEB medium (see, DNA Cloning, Vol. 2, p. 78) with shaking (28° C., 200 rpm). The culture was diluted 20-fold with sterilized water, and cocultured with petunia (Surfinia) leaf disks. After 2 to 3-day culturing, the bacterium was eliminated in the medium containing antibiotics, and the medium was replaced every other week. Kanamycin resistance conferred by expression of the NPTII gene derived from pBINPLUS introduced with the aforementioned fusion gene was used to select transformed petunia cells. Calli were derived from the selected cells, and then regenerated into plants according to a conventional method (Jorgensen, et al. (1996) Plant Mol. Biol. 31, 957-973).

Example 4

Expression of the ZPT2-3 Gene in ZPT2-3 Transformants

Figure 2:
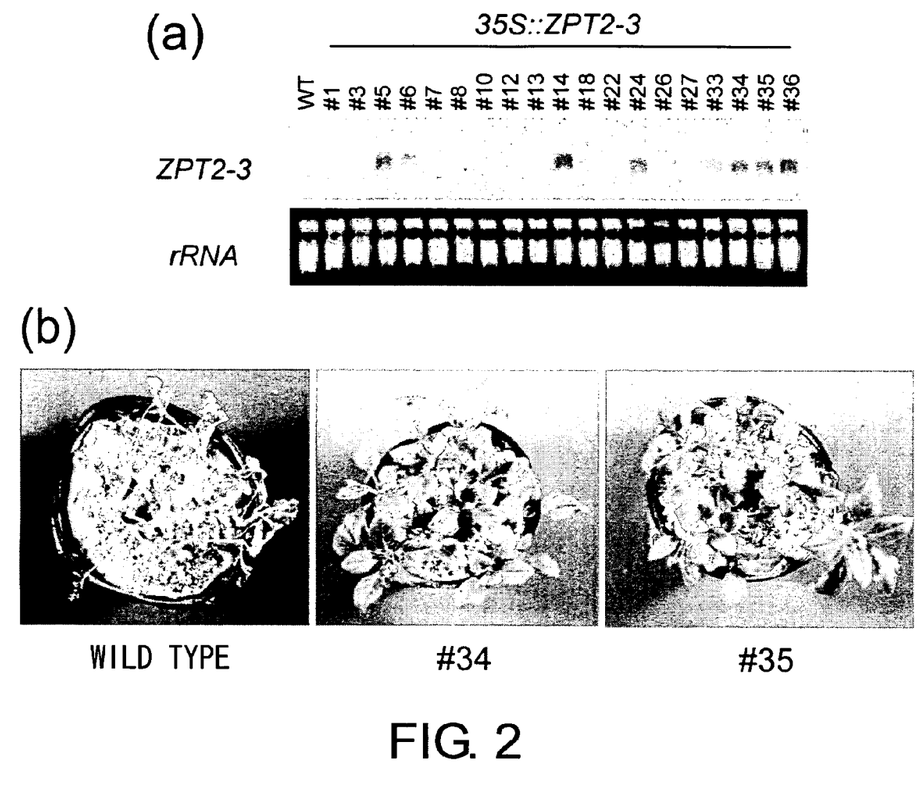
FIG. 2 shows photographs indicating that desiccation tolerance was increased as a result of ZPT2-3 gene overexpression.

Total RNAs were extracted from wild-type petunia and 19 lines of petunia transformants introduced and expressed with the ZPT2-3 gene. A 10-μg aliquot of each RNA was electrophoresed on an agarose gel, and blotted onto a Genescreen-plus filter. The result of hybridization using a ZPT2-3 antisense RNA labeled with the DIG RNA Labeling kit (Boeringer Manheim) is shown in FIG. 2. This result showed that nine lines of transformants, #5, 6, 14, 22, 24, 33, 34, 35, and 36, were expressed the introduced ZPT2-3 gene at high levels.

Example 5

Desiccation Tolerance of ZPT2-3 Transformants

Non-transformants (wild type) and two lines (#34 and #35; FIG. 2a) of the transformants expressing the introduced ZPT2-3 gene at high levels were germinated in an artificial soil of perlite:vermiculite (1:1). After four weeks of cultivation by a conventional procedure, no water was given for 30 days as a desiccation treatment. At this point, all plants were withered. Watering was then resumed. After one week, the viability was determined. As the result shown in FIG. 2b, most transformants derived from the two lines recovered and grew normally again, while the non-transformants failed to recover, dried up, and died. Table 1 shows the viability in duplicate experiments.

TABLE 1

|  | LINE | NUMBER OF VIABLE SUBJECTS | TOTAL NUMBER OF SUBJECTS | VIABILITY (%) |
| --- | --- | --- | --- | --- |
| EXPERIMENT 1 | WILD TYPE | 5 | 20 | 25.0 |
|  | #34 | 19 | 20 | 95.0 |
|  | #35 | 17 | 20 | 85.0 |
| EXPERIMENT 2 | WILD TYPE | 0 | 18 | 0 |
|  | #34 | 17 | 18 | 94.4 |
|  | #35 | 18 | 18 | 100 |

The results described above show that the transformed petunia plants acquire desiccation tolerance when the ZPT2-3 gene is constitutively expressed under the control of the 35S promoter. Since these transformants exhibited neither growth abnormality nor morphological abnormality, it is thought that overexpression of the ZPT2-3 gene has little adverse effect on plant growth or such.

INDUSTRIAL APPLICABILITY

Plant desiccation tolerance can be increased by introducing the zinc finger transcription factor gene. The increased desiccation tolerance is expected to save labor in the cultivation of crops and garden plants. In addition, the present invention enables the expansion of crop cultivable area, and can thus provide a countermeasure against the problem of food shortage.

The invention claimed is:

1. A method for increasing desiccation tolerance in a plant, the method comprising:
   (I) transforming a plant cell with an expression vector into which the DNA of any one of (a) to (c) is inserted:
      (a) a DNA encoding a protein comprising the amino acid sequence of SEQ ID NO: 3;
      (b) a DNA comprising the coding region of the nucleotide sequence of SEQ ID NO: 2; and
      (c) a DNA encoding a protein comprising an amino acid sequence having at least 95% or higher sequence identity to SEQ ID NO: 3;
   (II) expressing the DNA of any one of (a) to (c) in the plant cell;
   (III) regenerating a transformed plant from the plant cell; and
   (IV) selecting for a transformed plant comprising said expression vector and having increased desiccation tolerance as determined by withholding water from the plant for thirty days, resuming watering after thirty days, and then selecting for the transformed plant that remains viable, thereby increasing desiccation tolerance in the transformed plant as compared to a plant of the same species lacking said expression vector.

2. The method of claim 1, further comprising preparing breeding material obtained from the transformed plant of claim 1, and wherein said breeding material comprises said expression vector.

3. The method of claim 1, wherein the DNA is selected from the group consisting of:
   (a) a DNA encoding a protein consisting of the amino acid sequence of SEQ ID NO: 3; and
   (b) a DNA comprising the coding region of the nucleotide sequence of SEQ ID NO: 2.

4. The method according to claim 1, wherein the transformed plant is a progeny or a clone obtained from the transformed plant, and wherein said progeny or clone comprises said expression vector.

* * * * *